(12) United States Patent
White et al.

(10) Patent No.: US 12,295,686 B2
(45) Date of Patent: May 13, 2025

(54) SYSTEM AND METHOD FOR ROBOTIC CART ARM ASSEMBLY IDENTIFICATION

(71) Applicant: Covidien LP, Mansfield, MA (US)

(72) Inventors: Nathan White, Hamden, CT (US); Edward Naclerio, Madison, CT (US)

(73) Assignee: Covidien LP, Mansfield, MA (US)

( * ) Notice: Subject to any disclaimer, the term of this patent is extended or adjusted under 35 U.S.C. 154(b) by 626 days.

(21) Appl. No.: 17/603,982

(22) PCT Filed: Jun. 12, 2019

(86) PCT No.: PCT/US2019/036677
§ 371 (c)(1),
(2) Date: Oct. 15, 2021

(87) PCT Pub. No.: WO2020/214194
PCT Pub. Date: Oct. 22, 2020

(65) Prior Publication Data
US 2022/0192770 A1     Jun. 23, 2022

Related U.S. Application Data

(60) Provisional application No. 62/833,850, filed on Apr. 15, 2019.

(51) Int. Cl.
*A61B 34/37* (2016.01)
*A61B 50/13* (2016.01)
(Continued)

(52) U.S. Cl.
CPC .............. *A61B 34/37* (2016.02); *A61B 50/13* (2016.02); *A61B 90/90* (2016.02); *G05D 1/0033* (2013.01)

(58) Field of Classification Search
None
See application file for complete search history.

(56) References Cited

U.S. PATENT DOCUMENTS 9,504,527 B2 * 11/2016 Smaby .................. A61B 34/20
2006/0149418 A1    7/2006 Anvari
(Continued)

FOREIGN PATENT DOCUMENTS

EP           3178436 A1    6/2017
WO        2010008126 A1    1/2010
(Continued)

OTHER PUBLICATIONS

International Search Report and Written Opinion dated Jan. 13, 2020 issued in corresponding PCT Appln. No. PCT/US2019/036677.
(Continued)

*Primary Examiner* — Jonathan L Sample
*Assistant Examiner* — Alan Lindsay Ostrow
(74) *Attorney, Agent, or Firm* — Carter, DeLuca & Farrel (57) ABSTRACT

A surgical robotic system includes a control tower having a first connector coupled to a first controller; and a movable robotic arm cart having a robotic arm and a second connector coupled to a second controller, the second connector being configured to couple to the first connector through a cable. The second controller being configured to transmit an identification signal having identification information of the movable robotic arm cart to the first controller to initialize the movable robotic arm cart for operation with the control tower.

20 Claims, 5 Drawing Sheets

(51) Int. Cl.
*A61B 90/90* (2016.01)
*G05D 1/00* (2006.01)

(56) References Cited

U.S. PATENT DOCUMENTS

| | | | |
|---|---|---|---|
| 2007/0075126 A1* | 4/2007 | Fu | G09G 5/006 |
| | | | 235/375 |
| 2009/0024120 A1 | 1/2009 | Sartor | |
| 2010/0125372 A1* | 5/2010 | Pietrzyk | G05B 19/058 |
| | | | 700/286 |
| 2011/0028969 A1 | 2/2011 | Sartor | |
| 2011/0276748 A1* | 11/2011 | Toyama | G06F 9/4403 |
| | | | 711/E12.008 |
| 2012/0316573 A1 | 12/2012 | Durant et al. | |
| 2013/0304944 A1* | 11/2013 | Young | G06F 9/4415 |
| | | | 710/16 |
| 2014/0128885 A1* | 5/2014 | Dachs | A61B 90/98 |
| | | | 606/130 |
| 2014/0128886 A1 | 5/2014 | Holop et al. | |
| 2014/0276951 A1 | 9/2014 | Hourtash et al. | |
| 2017/0165837 A1* | 6/2017 | Asano | A61B 34/30 |
| 2018/0360550 A1* | 12/2018 | Nakanishi | A61B 34/37 |
| 2018/0368920 A1 | 12/2018 | Ummalaneni | |
| 2019/0083186 A1 | 3/2019 | Zietlow et al. | |
| 2019/0125456 A1* | 5/2019 | Shelton, IV | A61B 17/072 |
| 2021/0055939 A1* | 2/2021 | Deng | G06F 9/44505 |

FOREIGN PATENT DOCUMENTS

| | | |
|---|---|---|
| WO | 2017098261 A1 | 6/2017 |
| WO | 2017210497 A1 | 12/2017 |

OTHER PUBLICATIONS

Extended European Search Report issued in corresponding application EP 19925075.4 dated Dec. 6, 2022 (10 pages).

Office Action issued in corresponding Chinese Application CN 201980001020.1 dated Nov. 22, 2023, together with English language translation (21 pages).

* cited by examiner

SYSTEM AND METHOD FOR ROBOTIC CART ARM ASSEMBLY IDENTIFICATION

CROSS-REFERENCE TO RELATED APPLICATION

This application is a National Stage Application under 35 U.S.C. § 371 (a) of PCT/US2019/36677, filed Jun. 12, 2019, which claims the benefit of and priority to U.S. Provisional Application No. 62/833,850, filed Apr. 15, 2019. The entire contents of all of the foregoing applications are incorporated by reference herein.

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within the patient's body.

Typically, the robotic arm is disposed on a cart, which allows a clinician to move the robotic arm to different locations within the operating room relative to a surgical table. Since the robotic arm can be moved, it is necessary to properly identify and align the robotic arm with the surgical table in order to ensure that movements of the robotic arm and the surgical instrument properly correlate to the location of the patient on the surgical table.

Accordingly, solutions are sought for overcoming the challenges involved in aligning the robotic arm with the surgical table, as well as verifying the compatibility of the robotic arm and devices to which the robotic arm is connected to.

SUMMARY

According to one embodiment of the present disclosure, a surgical robotic system includes a control tower having a first connector coupled to a first controller; and a movable robotic arm cart having a robotic arm and a second connector coupled to a second controller, the second connector being configured to couple to the first connector through a cable. The second controller being configured to transmit an identification signal having identification information of the movable robotic arm cart to the first controller to initialize the movable robotic arm cart for operation with the control tower.

According to another aspect of the above embodiment, the surgical robotic further includes an operating console coupled to the control tower and configured to transmit a control signal to the control tower, wherein the control tower is configured to, based on the control signal from the operating console, control the robotic arm after the movable robotic arm cart is initialized. The first controller is further configured to receive the identification signal from the second controller and, based on the identification signal, transmit a response signal to indicate that the first controller is configured to be coupled to the second controller.

According to a further aspect of the above embodiment, the first controller is further configured to receive the identification signal from the second controller and, based on the identification signal, transmit a response signal to indicate that the first controller is not configured to be coupled with the second controller. The second connector includes a plurality of contacts, a subset of which are reserved for communication by the second controller that, in response to receiving a power signal, transmit a predetermined identification signal. The identification signal is formed by a predetermined configuration of high and low signals, each of the high and low signals corresponding to a specific pin from among the plurality of contacts, the combination of the contacts and the high and low signals being associated with the identification signal. The contacts reserved for communication of the identification signal are general purpose input/output (GPIO) contacts. The GPIO contacts may be at least single fault tolerant. The GPIO includes four contacts, with two contacts of the four contacts configured to output a high signal and two contacts of the four contacts configured to output a low signal for identification of the movable robotic arm cart by the control tower.

According to another embodiment of the present disclosure, a method of identifying device mismatches in a surgical robotic system between a movable robotic arm cart and a control tower is disclosed. The method includes assigning an identification number at a first controller of a control tower to a movable robotic arm cart; transmitting from a second connector coupled to a second controller of the movable robotic arm cart, an identification signal based on the identification number assigned to the movable robotic arm cart; receiving the identification signal at a first connector coupled to the first controller of the control tower, the first connector operably coupled to the second connector by a cable; and determining, at the first controller, whether the identification signal matches the identification number.

According to one aspect of the above embodiment, the method further includes transmitting a control signal from the control tower to the movable robotic arm cart to initialize operation of the movable robotic arm cart by the control tower based on the determination by the first controller that the identification signal matches the identification number.

According to another aspect of the above embodiment, the method further includes transmitting an indication signal from the control tower to an operating console having a display, the indication signal causing the display to indicate a match or a mismatch based on determining whether the identification signal matches the identification number. The method further includes determining includes comparing the identification signal to indexed identification information stored in a memory of the second controller. The first connector and the second connector include a plurality of contacts that operate as general purpose input/output (GPIO) contacts for communicating with each other. The first controller of the control tower is configured to output an indication of the mismatch via the control tower or the movable robotic arm cart.

According to a further aspect of the above embodiment, causing an indication to be output includes displaying at least one of a serial number, model number, or connector number associated with the movable robotic arm cart via a display device of the operating console.

According to yet another embodiment of the present disclosure, a surgical robotic includes: a control tower having a first connector coupled to a first controller; and a movable robotic arm cart having a second connector coupled to a second controller, the second connector being configured to couple to the first connector through a cable. The first controller is configured to assign an identification number to the movable robotic arm cart and the second controller is configured to transmit an identification signal based on the identification number to the first controller, which is further configured to compare the identification number to the identification signal.

According to one aspect of the above embodiment, the first controller is further configured to receive the identification signal from the second controller and, based on the identification signal, transmit a response signal to indicate that the first controller is not configured to be coupled with the second controller. The second connector includes a plurality of contacts, a subset of which are reserved for communication by the second controller that, in response to receiving a power signal, transmit a predetermined identification signal. The identification signal is formed by a predetermined configuration of high and low signals, each of the high and low signals corresponding to a specific pin from among the plurality of contacts, the combination of the contacts and the high and low signals being associated with the identification signal. The contacts reserved for communication of the identification signal are general purpose input/output (GPIO) contacts. The GPIO contacts may be at least single fault tolerant. The GPIO includes four contacts, with two contacts of the four contacts configured to output a high signal and two contacts of the four contacts configured to output a low signal for identification of the movable robotic arm cart by the control tower.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

Although the following description is specific to a surgical robotic system, the disclosed systems and methods may be implemented with any suitable medical device which would otherwise be within the scope of the present disclosure.

As will be described in detail below, the present disclosure is directed to a surgical robotic system, which, in embodiments, includes a surgical console, a control tower, and one or more surgical robotic arms coupled to a setup arm. The surgical console is used to receive user input through one or more interface devices, which are interpreted by the control tower as movement commands for moving the surgical robotic arm. The surgical robotic arm includes a controller, which is configured to process the movement command and to generate a torque command for activating one or more actuators, which would, in turn, move the surgical arm in response to the movement command.

The surgical console and one or more surgical robotic arms are connected to the control tower which acts as a centralized command center and operations control as well as provides power to each of the connected components. Upon connection of each of the components to the control tower, the control tower assigns an identification number to each of the components, which may be embodied as a 4-bit value. Each of the bits corresponds to a pin of a connector of the components, which output an identification signal to the control tower. The control tower continuously receives the 4-bit value corresponding to the assigned identification number as the identification signal. The control tower also compares the received identification signal to the assigned identification number to determine if the two values are the same to confirm that the connection is functional, i.e., the connectors are properly outputting the identification signals.

Figure 1:
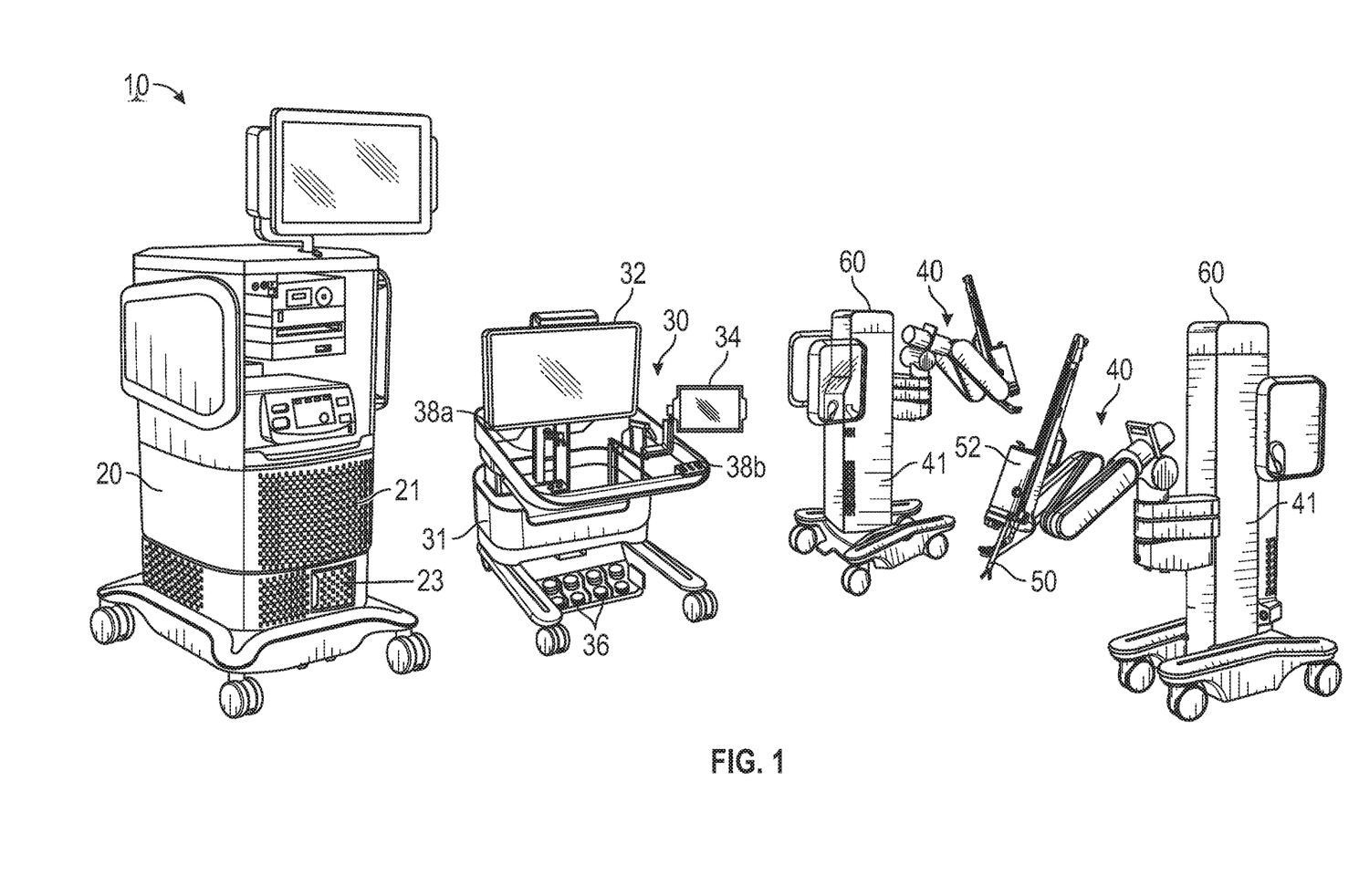
FIG. 1 is a schematic illustration of a surgical robotic system including a control tower, a console, and one or more surgical robotic arms according to the present disclosure.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. The surgical instrument 50 is configured for use during minimally invasive surgical procedures. In embodiments, the surgical instrument 50 may be configured for open surgical procedures. Each of the robotic arms 40 is also coupled to a movable cart 60.

The surgical console 30 includes a first display device 32, which displays a surgical site provided by cameras (not shown) disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38b which are used by a clinician to remotely control robotic arms 40.

The control tower 20 acts as an interface between the surgical console 30 and one or more robotic arms 40. In particular, the control tower 20 is configured to control the robotic arms 40, such as to move the robotic arms 40 and the corresponding surgical devices 50, based on a set of programmable instructions and/or input commands from the surgical console 30, in such a way that robotic arms 40 and the surgical device 50 execute a desired movement sequence in response to input from the foot pedals 36 and the handle controllers 38a and 38b.

The control tower 20 also includes a power supply 23 configured to provide electrical power to all of the components of the surgical robotic system 10, namely, the control tower 20 itself, the surgical console 30, and one or more robotic arms 40. In embodiments, the power supply 23 may be a standalone device and may have any suitable form factor such as a tower and may be stationary or mobile (e.g., include wheels). In embodiments, the power supply 23 may include any suitable power generating or converting circuit components configured to generate either AC and/or DC power. Where the power supply 23 is configured to generate AC power, the power supply 23 may be further configured to generate radio frequency (RF) or microwave power suitable for performing electrosurgical procedures such as vessel sealing, cutting, coagulation, ablation, etc. In embodiments, where the power supply 23 is configured to generate DC power, the power supply 23 may be used to provide electrical power to actuate motors and other actuators of powered surgical devices, such as powered staplers, graspers, cutters, robotic arms 40, etc.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
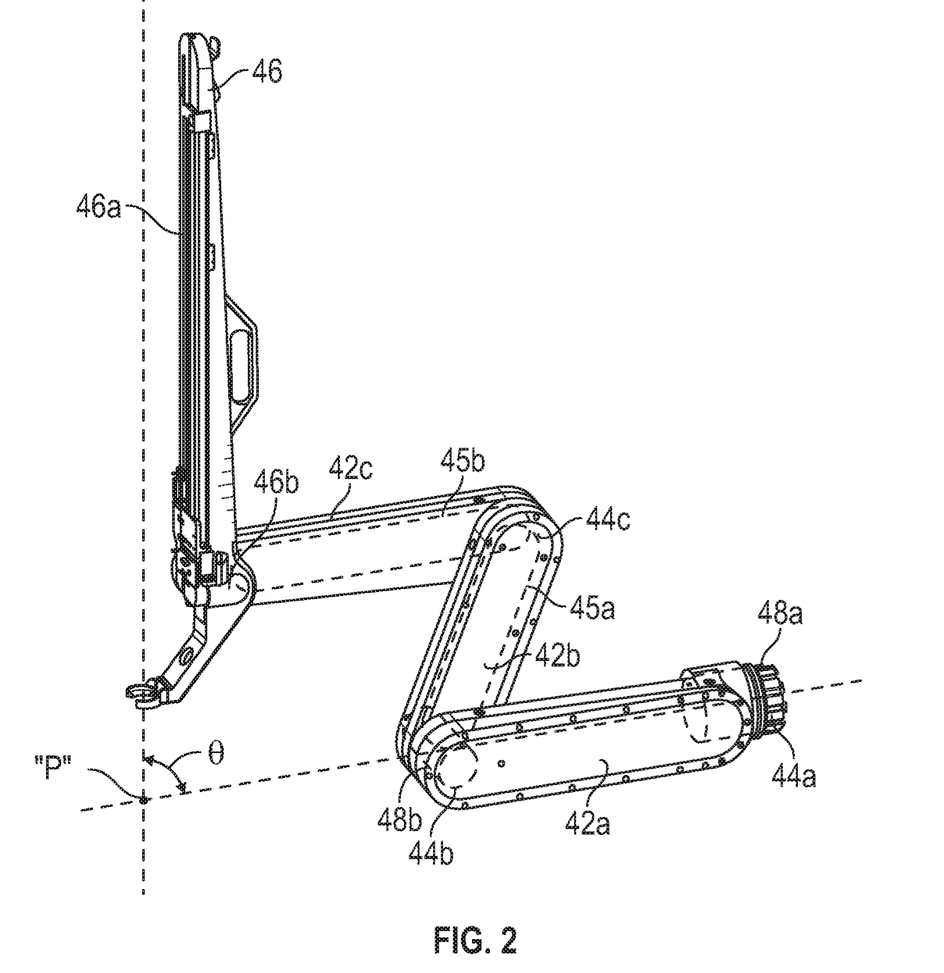
FIG. 2 is a perspective view of a surgical robotic arm of the surgical robotic system of FIG. 1 according to the present disclosure.
Figure 3:
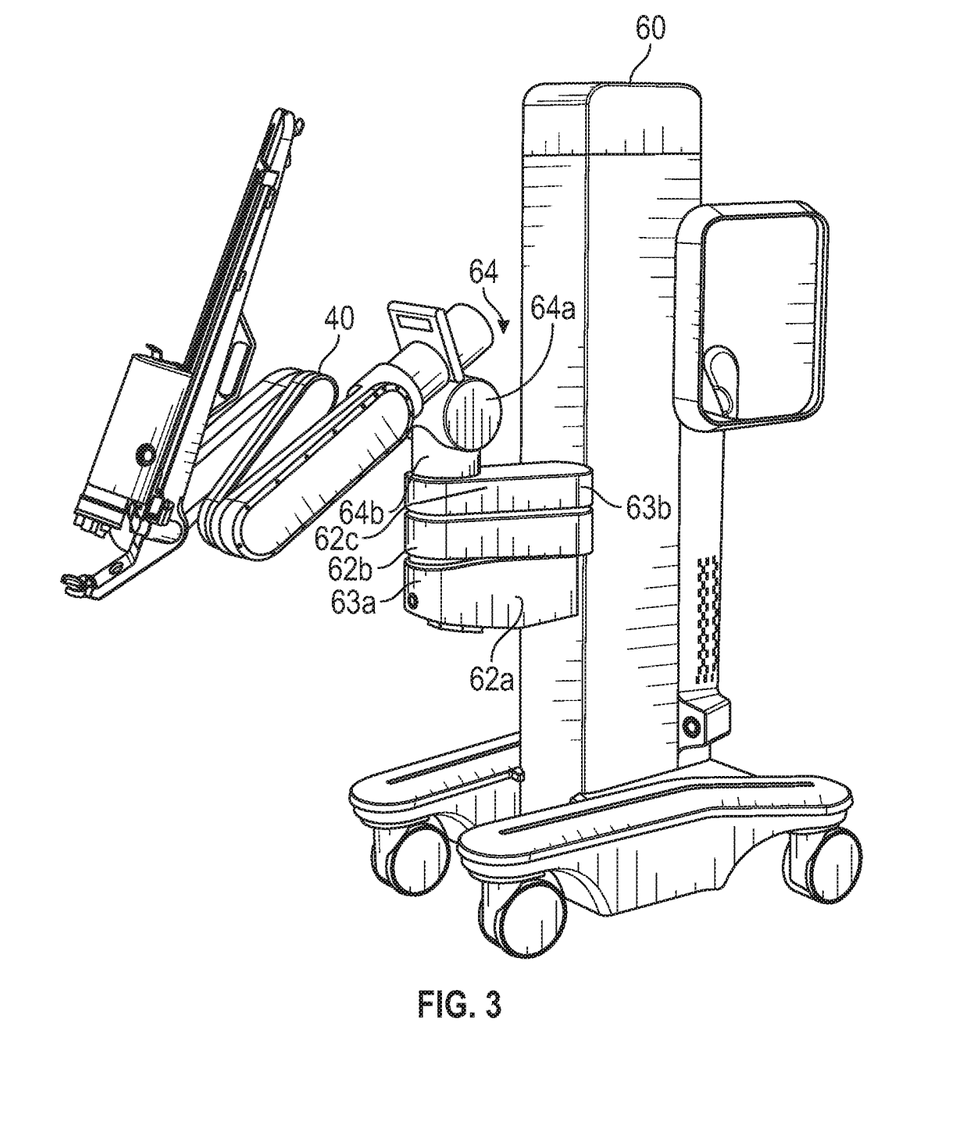
FIG. 3 is a perspective view of a setup arm with the surgical robotic arm of the surgical robotic system of FIG. 1 according to the present disclosure.

With reference to FIG. 2, each of the robotic arms 40 may include of a plurality of links 42a, 42b, 42c, which are interconnected at rotational joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The setup arm 62 includes a first link 62a, a second link 62b, and a third link 62c, which provide for lateral maneuverability of the robotic arm 40. The links 62a, 62b, 62c are interconnected at rotational joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is parallel to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a rotational joint 46b, which rotates the holder 46 relative to the link 42c.

The joints 44a and 44b include an electrical actuator 48a and 48b configured to drive the joints 44a, 44b, 44c relative to each other through a series of belts 45a and 45b or other mechanical linkages such as a drive rod, a cable, or a lever and the like. In particular, the actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an electrical actuator to obviate the need for mechanical linkages.

Figure 4:
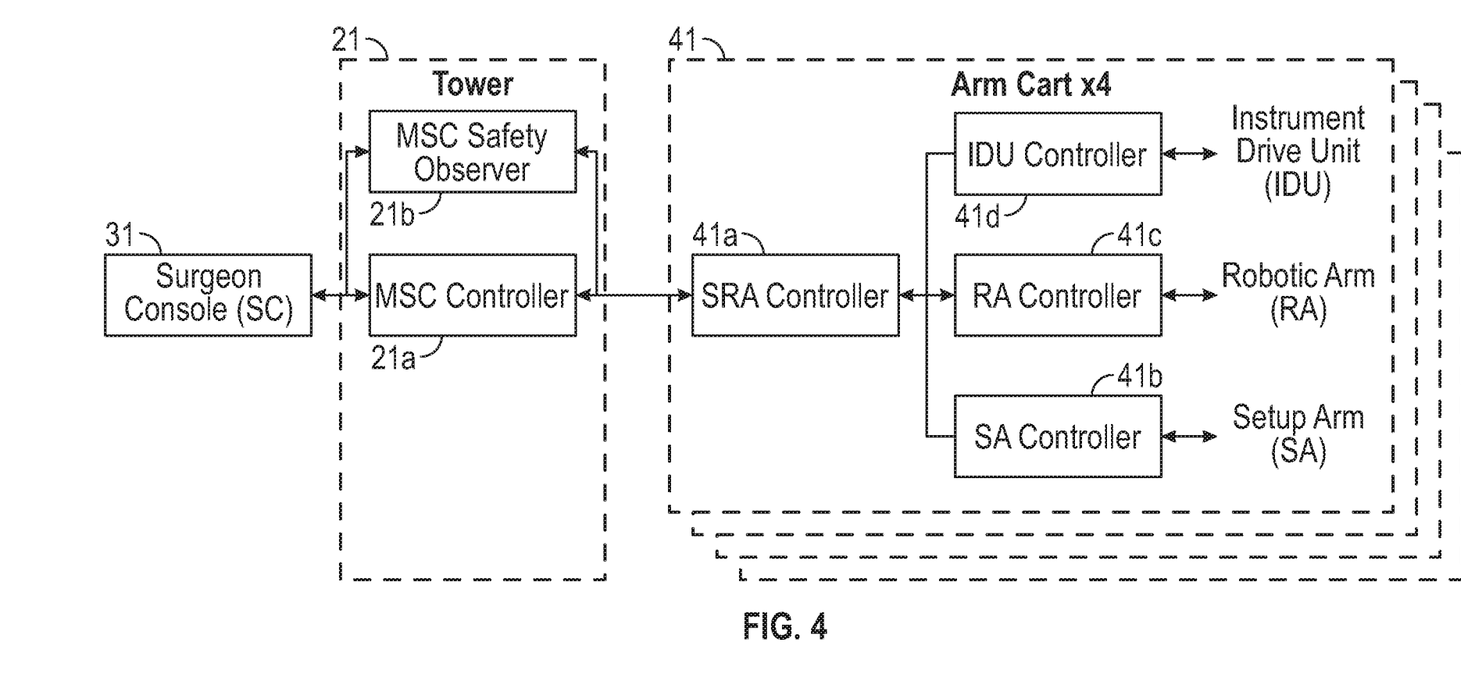
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical system 10 into a safe state.

The computer 41 includes a plurality of controllers, namely, a main controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the instrument drive unit 52. The main cart controller 41a also communicates actual joint angles back to the controller 21a.

The setup arm controller 41b controls each of rotational joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation and closed loop position control. The robotic arm controller 41c calculates a movement command based on the calculated torque. The calculated motor commands are then communicated to one or more of the electrical actuators 48a and 48b in the robotic arm 40. The actual joint positions are then transmitted by the electrical actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits these back to the main controller 41a.

Figure 5:
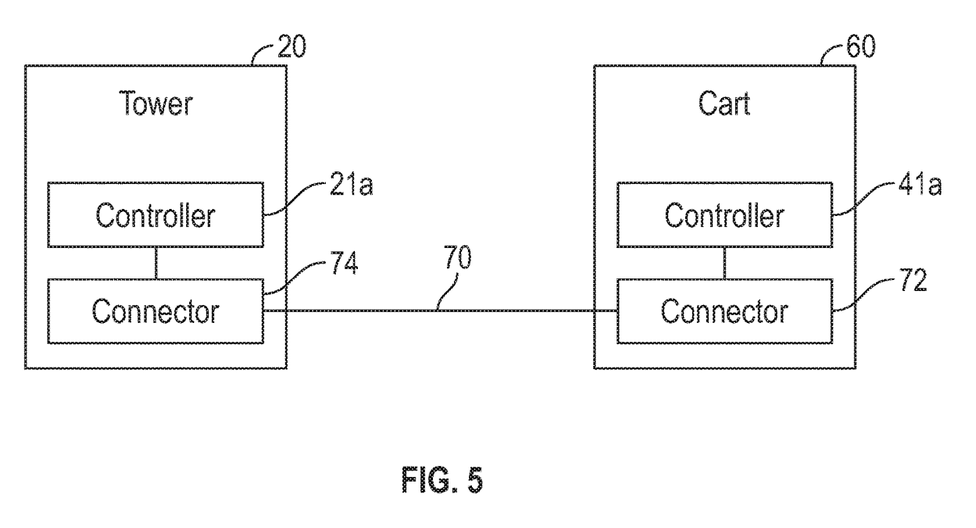
FIG. 5 is a schematic diagram of a connection between the control tower and the surgical robotic arm.

With reference to FIG. 5, the movable cart 60 is coupled to the power supply 23 of the tower 20 via a multi-conductor cable 70 and is used to supply electrical energy to the movable cart from the power supply 23 of the tower 20. Specifically, the movable cart 60 includes a connector 72 configured to couple to the cable 70 to enable electrical communication between the movable cart 60 and the tower 20. The cable 70 is also coupled to a connector 74 of the tower 20. Although only the connection between the movable cart 60 and the tower 20 is described below, it is envisioned that a similar connection and identification scheme may be used with any component of the system 10, including the surgical console 30.

The connector 72 may be coupled to, or otherwise in communication with the main cart controller 41a of the movable cart 60 and the connector 74 is coupled to the controller 21a of the tower 20. The connectors 72 and 74 may be any suitable general purpose input/output connector (GPIO), and in embodiments include a plurality of contacts (not shown) configured to transmit and/or receive electrical signals. As used herein, contacts of the connectors described throughout the application reserved for general purpose communication are referred to as a GPIO and may include any number of contacts disposed in any configuration.

In embodiments, the tower 20, and in particular, the controller 21a, assigns a unique identification number (Component ID) to the movable cart 60, when the movable cart 60 is initially connected to the tower 20. The identification number may be a 4-bit value, each of the bits corresponding to each of the contacts of the connectors 72 and 74. In embodiments, the identification number may be any binary value, with each of the bits corresponding to a contact of the connectors 72 and 74.

In embodiments, once the cable 70 is coupled to the connectors 72 and 74 of both the tower 20 and the movable cart 60, respectively, the tower 20 assigns the unique identification number (Component ID) and transmits identification number to the movable cart 60 (assigning the movable cart 60 a Component ID). In response, or upon subsequent connection, a predetermined amount of contacts may be energized by the main controller 41a of the movable cart 60 to enable the tower 20 to identify the movable cart 60 (e.g., a first and third pin of a four plus pin connector ("0101")). The amount of contacts reserved and set to either high "1" or low "0" may be any suitable number, depending on the amount of available components (e.g., movable carts 60) included in the surgical robotic system 100, number of conductors in the cable 70, etc. If the system 10 includes four movable carts 60, each movable cart 60 may receive a unique identification signal from the tower 20 transmitted during initialization (e.g., Component ID 1="1100"; Component ID 2="1010"; Component ID 3="0101"; Component ID 4="0011"; etc.). If the tower 20, upon later receiving a signal including the identification signal from the movable cart 60, determines that the connector 74 of the tower 20 is preconfigured to couple to the movable cart 60 (e.g., the Component ID matches the assigned Component ID), the tower 20 continues with the operation and control of the movable cart 60, as well as the components connected thereto, e.g., the surgical robotic arm 40.

Upon initial connection and receipt of the unique identification number, the main controller 41a stores the unique identification number in memory. Upon subsequent connection to the tower 20, the main controller 41a of the movable cart 60 may transmit the unique identification number to the tower 20 to identify the movable cart 60. The initial assignment of the unique identification number to the movable cart 60 may further associate the movable cart 60 with a particular connector 74 of the tower 20. In embodiments, once the movable cart 60 is disconnected from the tower 20 and/or power of either the tower 20 or the movable cart 60 is cycled (e.g., the tower 20 and/or movable cart 60 is turned off and on again) the tower 20, upon reconnection to the movable cart 60, may assign a new unique identification number to the movable cart 60. In embodiments, the movable cart 60 may be assigned a unique identification number prior to each initialization (e.g., every time the tower 20 is connected to the movable cart 60). Each subsequent movable arm 60 that is connected to the tower 20 is assigned a unique identification number.

In embodiments, the main controller 41a of the movable cart 60, upon connection (either directly or operably) to the tower 20, may transmit a signal (e.g., the identification signal) including identification information signal including the assigned identification number as well as make, model, and/or serial number of the movable cart 60 and/or the surgical robotic arm 40. This identification information signal transmitted by the movable cart 60 to the tower 20 may be used by the tower 20 to confirm the identification number associated with the movable cart 60 (e.g., for the particular functions the movable cart 60 is capable of performing). In embodiments, the movable cart 60 may include an internal power supply (e.g., a battery) coupled to the logic circuit and/or to the connector 72 directly, though in embodiments the following may occur in response to receiving an initial electric signal at the connector 72. Initialization signals may be sent by the tower 20 to the movable cart 60 to provide the various components (e.g., the robotic arm 40) of the movable cart 60 with identification information signal.

In embodiments where the tower 20 receives an identification signal from the movable cart 60 upon subsequent connection (e.g., when the movable cart 60 is disconnected and reconnected), the tower 20 may compare the identification signal (e.g., the Component ID) to a lookup table including assigned identification numbers. The lookup table may include an index of all device identification numbers assigned by the tower 20 as well as corresponding connectors 74 to which the devices were coupled to when the tower 20 assigned the identification numbers (e.g., the Component IDs) to the movable carts 60. The identification signal may include identification information signal such as, without limitation, a serial number, model number, etc., of the movable cart 60. If the identification information signal is matched with the identification number (e.g., where a device match exists), the tower 20 may continue with the initialization process, and configure the movable cart 60 for a surgical procedure. Alternatively, if the identification information signal is not matched with the identification number information signal (e.g., where a device mismatch exists), the tower 20 may take no action or cause an error warning to be output by either the tower 20, the movable cart 60, or the surgical console 30.

The tower 20 may terminate the initialization process and/or operation of the movable cart 60 if disconnected from the connector 74 of the tower 20. If the movable cart 60 is later reconnected to the tower 20 at the same connector 74, or to another connector 74, the movable cart 60 may either verify the connection (where the Component ID matches the previously-assigned Component ID for that connector 74) or reiterate the initialization process and assign new identification information signal (a new Component ID) to the movable cart 60. If the connection is terminated, the tower 20 may further output an error signal, which may be displayed on the surgical console 30. In embodiments, in response to this initial determination whether the movable cart 60 is connected to the appropriate connector 74 of the tower 20, mismatches and unintended connections may be identified early in the configuration process, thereby reducing the setup time necessary to prepare the surgical robotic system 10 and/or swap out movable carts 60 during surgical procedures.

In further embodiments, fault-tolerance may be built into the initialization process. Particularly, upon initial connection, if a mismatch is detected (either in error or otherwise) based on the initial identification signal, the tower 20 may either request and/or receive a second identification signal from the movable cart 60. This fault-tolerance may include retransmitting the identification information signal from the tower 20 a plurality of times and determining, upon each retransmission, whether the identification signals received from the movable cart 60 by the tower 20 were received by the movable cart 60.

After initialization, namely, after assignment of the identification number to each of the movable carts 60, as long as the movable carts 60 are connected to the tower 20, each of the movable carts 60 continuously transmits the assigned identification number to the tower 20 through the contacts of the cable 70. Any disruption or mismatch in the identification number is interpreted by the tower 20 as a failure in the connectors 72, 74, and/or cable 70. This allows for almost immediate (i.e., accounting for any latency in transmission of the identification signal) verification of the loss of connection of the tower 20 and the movable cart 60 and/or surgical console 30 through the cable 70.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a control tower having a first connector coupled to a first controller; and
a movable robotic arm cart having a robotic arm and a second connector coupled to a second controller, the second connector being configured to couple to the first connector through a cable,
wherein the first controller is configured to assign a unique identification number to the movable robotic arm cart upon initial connection of the movable robotic arm cart to the control tower via the cable coupled to the first connector and the second connector, and the second controller being configured to continuously transmit an identification signal having identification information of the movable robotic arm cart including the assigned identification number to the first controller to initialize the movable robotic arm cart for operation with the control tower, and
wherein the first controller is further configured to continuously receive the transmitted identification signal having the identification information, and compare the identification information to the assigned identification number to determine whether the identification information and the assigned identification number are the same to confirm that a connection between the movable robotic arm cart and the control tower is functional.

2. The surgical robotic system of claim 1, further comprising:
an operating console coupled to the control tower and configured to transmit a control signal to the control tower, wherein the control tower is configured to, based on the control signal from the operating console, control the robotic arm after the movable robotic arm cart is initialized.

3. The surgical robotic system of claim 1, wherein the first controller is configured to receive the identification signal from the second controller and, based on the identification signal, transmit a response signal to indicate that the first controller is configured to be coupled to the second controller.

4. The surgical robotic system of claim 1, wherein the first controller is configured to receive the identification signal from the second controller and, based on the identification signal, transmit a response signal to indicate that the first controller is not configured to be coupled with the second controller.

5. The surgical robotic system of claim 4, wherein the second connector includes a plurality of contacts, a subset of which are reserved for communication by the second controller that, in response to receiving a power signal, transmit a predetermined identification signal.

6. The surgical robotic system of claim 5, wherein the identification signal is formed by a predetermined configuration of high and low signals, each of the high and low signals corresponding to a specific pin from among the plurality of contacts, the combination of the contacts and the high and low signals being associated with the identification signal.

7. The surgical robotic system of claim 5, wherein the contacts reserved for communication of the identification signal are general purpose input/output (GPIO) contacts.

8. The surgical robotic system of claim 7, wherein the GPIO contacts are at least single fault tolerant.

9. The surgical robotic system of claim 7, wherein the GPIO includes four contacts, with two contacts of the four contacts configured to output a high signal and two contacts of the four contacts configured to output a low signal for identification of the movable robotic arm cart by the control tower.

10. A method of identifying device mismatches in a surgical robotic system between a movable robotic arm cart and a control tower, the method comprising:
assigning a unique identification number at a first controller of a control tower to a movable robotic arm cart upon initial connection of the movable robotic arm cart to the control tower via a cable coupled to a first connector of the control tower and a second connector of the robotic arm cart;
continuously transmitting from the second connector coupled to a second controller of the movable robotic arm cart, an identification signal based on the identification number assigned to the movable robotic arm cart;
continuously receiving the identification signal at the first connector coupled to the first controller of the control tower, the first connector operably coupled to the second connector by the cable; and
continuously determining, at the first controller, whether the identification signal matches the identification number to confirm that a connection between the movable robotic arm cart and the control tower is functional.

11. The method of claim 10, further comprising:
transmitting a control signal from the control tower to the movable robotic arm cart to initialize operation of the movable robotic arm cart by the control tower based on the determination by the first controller that the identification signal matches the identification number.

12. The method of claim 10, further comprising transmitting an indication signal from the control tower to an operating console having a display, the indication signal causing the display to indicate a match or a mismatch based on determining whether the identification signal matches the identification number.

13. The method of claim 12, wherein determining includes comparing the identification signal to indexed identification information stored in a memory of the second controller.

14. The method of claim 13, wherein the first connector and the second connector include a plurality of contacts that operate as general purpose input/output (GPIO) contacts for communicating with each other.

15. The method of claim 14, wherein the first controller of the control tower is configured to output an indication of the mismatch via the control tower or the movable robotic arm cart.

16. The method of claim 12, wherein causing an indication to be output includes displaying at least one of a serial number, model number, or connector number associated with the movable robotic arm cart via a display device of the operating console.

17. A surgical robotic system comprising:
a control tower having a first connector coupled to a first controller; and
a plurality of movable robotic arm carts each having a second connector coupled to a second controller, the second connector being configured to couple to the first connector through a cable, wherein the first controller is configured to assign a unique identification number to each movable cart of the plurality of movable robotic arm carts upon initial connection of each movable cart of the plurality of movable robotic arm carts to the control tower via the cable coupled to the first connector and the second connector, and the second controller is configured to continuously transmit an identification signal having identification information of each movable cart of the plurality of movable robotic arm carts including the assigned identification number to the first controller, which is further configured to compare the assigned identification number to the identification information to determine whether the identification information and the assigned identification number are the same to confirm that a connection between each movable robotic arm cart of the plurality of the movable robotic arm carts and the control tower is functional.

18. The surgical robotic system of claim 17, wherein the first controller is configured to receive the identification signal from the second controller and, based on the identification signal, transmit a response signal to indicate that the first controller is not configured to be coupled with the second controller.

19. The surgical robotic system of claim 18, wherein the second connector includes a plurality of contacts, a subset of which are reserved for communication by the second controller that, in response to receiving a power signal, transmit a predetermined identification signal.

20. The surgical robotic system of claim 19, wherein the identification signal is formed by a predetermined configuration of high and low signals, each of the high and low signals corresponding to a specific pin from among the plurality of contacts, the combination of the contacts and the high and low signals being associated with the identification signal.

* * * * *